US012125598B2

(12) United States Patent
Lehmuth et al.

(10) Patent No.: US 12,125,598 B2
(45) Date of Patent: *Oct. 22, 2024

(54) NEURAL NETWORK ARTIFICIAL INTELLIGENCE SYSTEM FOR CLASS-BASED MODELING

(71) Applicant: Express Scripts Strategic Development, Inc., St. Louis, MO (US)

(72) Inventors: Christopher G. Lehmuth, St. Louis, MO (US); Alexi E. Makarkin, Ballwin, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/144,330

(22) Filed: May 8, 2023

(65) Prior Publication Data
US 2023/0274845 A1    Aug. 31, 2023

Related U.S. Application Data

(63) Continuation of application No. 16/511,833, filed on Jul. 15, 2019, now Pat. No. 11,657,922.

(51) Int. Cl.
*G16H 70/40* (2018.01)
*G16H 50/20* (2018.01)

(52) U.S. Cl.
CPC .............. *G16H 70/40* (2018.01); *G16H 50/20* (2018.01)

(58) Field of Classification Search
CPC ........ G16H 70/40; G16H 50/20; G16H 15/00; G16H 70/20; G16H 20/10; G16H 50/70
See application file for complete search history.

(56) References Cited

U.S. PATENT DOCUMENTS 7,246,083 B2    7/2007    Bibelnieks
8,112,287 B1    2/2012    Paul
(Continued)

OTHER PUBLICATIONS

Zhou, Siting, "Chronic Medication Adherence: It's Association with Health Care Costs", Graduate School of the University of Minnesota, ProQuest Dissertations Publishing, (2001) (Year: 2001).*
(Continued)

*Primary Examiner* — Amber A Misiaszek
(74) *Attorney, Agent, or Firm* — Miller Johnson

(57) ABSTRACT

A method includes receiving historical data collected from a client associated with members. The historical data includes per-member metrics for the client and demographic information for the members. The method includes identifying therapeutic classes for the client based on the per-member metrics and the demographic information. The method includes segmenting the historical data into a data set for each therapeutic class. The method includes, for each therapeutic class of the set of therapeutic classes, determining a pattern for the per-member metrics corresponding to the respective therapeutic class, generating a respective predictive model based on the pattern, and training a neural network of the respective predictive model using a two-stage training process. The predictive model is configured to generate, as output for the therapeutic class, a per-member metric prediction for an input period of future time. The method includes generating predictions for the therapeutic classes using the predictive models.

20 Claims, 10 Drawing Sheets

(56) References Cited

U.S. PATENT DOCUMENTS

| | | | |
|---|---|---|---|
| 8,112,288 B1 * | 2/2012 | Paul | G16H 20/10 |
| | | | 705/2 |
| 8,239,213 B1 * | 8/2012 | Paul | G06Q 10/10 |
| | | | 705/2 |
| 9,366,704 B2 | 6/2016 | Haghighat-Kashani | |
| 2006/0218010 A1 | 9/2006 | Michon | |
| 2012/0303382 A1 | 11/2012 | Paul | |
| 2013/0297349 A1 | 11/2013 | Epstein | |
| 2014/0200954 A1 * | 7/2014 | Trifunov | G16H 10/20 |
| | | | 705/7.28 |
| 2016/0335412 A1 | 11/2016 | Tucker | |
| 2017/0032255 A1 | 2/2017 | Chandra | |
| 2017/0323078 A1 | 11/2017 | Michon | |
| 2018/0189691 A1 | 7/2018 | Oehrle | |
| 2018/0218051 A1 * | 8/2018 | Berger | G06F 16/951 |
| 2019/0080416 A1 | 3/2019 | Smith | |
| 2019/0115097 A1 | 4/2019 | Macoviak | |

OTHER PUBLICATIONS

Zhou, Siting, "Chronic Medication Adherence: It's Association with Health Care Costs", Graduate School of the University of Minnesota, ProQuest Dissertations Publishing, (2011 ). (Year: 2011).

* cited by examiner

NEURAL NETWORK ARTIFICIAL INTELLIGENCE SYSTEM FOR CLASS-BASED MODELING

CROSS-REFERENCE TO RELATED APPLICATIONS

This application is a continuation of U.S. patent application Ser. No. 16/511,833 filed Jul. 15, 2019 (now U.S. Pat. No. 11,657,922), the entire disclosure of which is incorporated by reference.

FIELD

The present disclosure relates generally to computerized healthcare systems and methods and more particularly to artificial intelligence systems for healthcare data management.

BACKGROUND

Organizations such as health plan managers and pharmacy benefit managers (PBMs) need help in caring for their plan members and making medicine affordable to their plan members. These clients can benefit from systems and methods that provide solutions for improving member care and reducing costs of member care. A low value for drug trend, where drug trend may be measured as year-over-year change in drug spending, and decreases in drug spending, where drug spending may be measured per member per month (PMPM) spending, help health plans to profitably maintain meaningful and affordable health benefits.

For health plans to be profitable, their PMPM spending needs to be well below their monthly premiums. PMPM spending may be calculated as a ratio of total monthly spending for a group of members to the number of members in the group. PMPM spending depends on unit cost and unit volume. A scarcely used expensive drug may result in less total spending than a frequently used inexpensive drug. PMPM spending can be reduced by lowering unit cost, unit volume, or both. Approaches for lowering unit cost include obtaining rebates from pharmaceutical companies, lowering payments to pharmacies, and so on. Unit volume can be managed through control techniques such as requiring prior authorization. Accordingly, forecasting drug trend and PMPM spending can be very helpful to health plan managers in lowering drug trend and reducing PMPM spending, and increasing profitability while providing affordable and improved healthcare benefits to their members.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A method for generating predictions for year-over-year change in drug spending and per member per month spending and for providing the predictions via a web portal is presented. The method includes receiving data collected from a health plan, where the data includes per member per month costs of the health plan and demographic information of members of the health plan. The method further includes selecting therapeutic classes based on the per member per month costs and demographic information, segmenting the data by the therapeutic classes, and detecting patterns by analyzing the segmented data. The method further includes generating models for the therapeutic classes based on the patterns, and generating predictions for year-over-year change in drug spending and per member per month spending for the therapeutic classes by utilizing the models. The method further includes providing the predictions via a web portal in at least one of a displayable graphical format and a downloadable data structure.

In other features, the predictions are further categorized for brand name, generic, and specialty drugs for each of the therapeutic classes.

In other features, the method further includes training the models using first data collected from the health plan over a first time period, and validating the trained models using second data collected from the health plan over a second time period. The first time period is longer in duration and older than the second time period.

In other features, the method further includes collecting additional data about new drugs to be released and about impact in the past of release of other new drugs on year-over-year change in drug spending and on per member per month spending, and training the models using the additional data.

In other features, the method further includes training the validated models using the first data and the second data, and generating the predictions using the trained validated models.

In other features, the method further includes reconfiguring one of the models in response to the one of the models failing validation, retraining all of the models including the reconfigured model using the first data, and revalidating, subsequent to the retraining, all of the models including the reconfigured model using the second data.

In other features, the method further includes generating a new model to replace one of the models in response to the one of the models failing validation due to an anomaly, and using the new model to generate a portion of the predictions.

Additionally, a non-transitory computer-readable medium storing processor-executable instructions for generating predictions for year-over-year change in drug spending and per member per month spending and for providing the predictions via a web portal is presented. The instructions include receiving data collected from a health plan, where the data includes per member per month costs of the health plan and demographic information of members of the health plan. The instructions further include selecting therapeutic classes based on the per member per month costs and demographic information, segmenting the data by the therapeutic classes, and detecting patterns by analyzing the segmented data. The instructions further include generating models for the therapeutic classes based on the patterns, and generating predictions for year-over-year change in drug spending and per member per month spending for the therapeutic classes by utilizing the models. The instructions further include providing the predictions via a web portal, in a displayable graphical format, as downloadable data, or both, to allow a benefit manager of the health plan to selectively adjust the health plan based on the predictions to profitably offer improved healthcare benefits to the members of the health plan.

In other features, the predictions are further categorized for brand name, generic, and specialty drugs for each of the therapeutic classes.

In other features, the instructions further include training the models using first data collected from the health plan over a first time period, and validating the trained models using second data collected from the health plan over a second time period. The first time period is longer in duration and older than the second time period.

In other features, the instructions further include collecting additional data about new drugs to be released and about impact in the past of release of other new drugs on year-over-year change in drug spending and on per member per month spending, and training the models using the additional data.

In other features, the instructions further include training the validated models using the first data and the second data, and generating the predictions using the trained validated models.

In other features, the instructions further include reconfiguring one of the models in response to the one of the models failing validation, retraining all of the models including the reconfigured model using the first data, and revalidating, subsequent to the retraining, all of the models including the reconfigured model using the second data.

In other features, the instructions further include generating a new model to replace one of the models in response to the one of the models failing validation due to an anomaly, and using the new model to generate a portion of the predictions.

In addition, a system for generating predictions for year-over-year change in drug spending and per member per month spending and for providing the predictions via a web portal is presented. The system includes a data acquisition circuit configured to receive data collected from a health plan, where the data includes per member per month costs of the health plan and demographic information of members of the health plan. The system further includes a data segmenting circuit configured to select therapeutic classes based on the per member per month costs and demographic information, and to segment the data by the therapeutic classes. The system further includes a model generating circuit configured to detect patterns by analyzing the segmented data, and to generate models for the therapeutic classes based on the patterns. The system further includes a prediction circuit configured to generate predictions for year-over-year change in drug spending and per member per month spending for the therapeutic classes by utilizing the models. The predictions are further categorized for brand name, generic, and specialty drugs for each of the therapeutic classes. The prediction circuit is further configured to provide the predictions via a web portal, in a displayable graphical format, as downloadable data, or both, to allow a benefit manager of the health plan to selectively adjust the health plan based on the predictions to profitably offer improved healthcare benefits to the members of the health plan.

In other features, the system further includes a model training circuit configured to train the models using first data collected from the health plan over a first time period, and a model validating circuit configured to validate the trained models using second data collected from the health plan over a second time period. The first time period is longer in duration and older than the second time period.

In other features, the system further includes a pipeline predicting circuit configured to collect additional data about new drugs to be released, and to predict impact in the past of release of other new drugs on year-over-year change in drug spending and on per member per month spending. The model training circuit is configured to train the models using the additional data.

In other features, the model training circuit is configured to train the validated models using the first data and the second data, and the prediction circuit is configured to generate the predictions using the trained validated models.

In other features, the model training circuit is configured to reconfigure one of the models in response to the one of the models failing validation, and to retrain all of the models including the reconfigured model using the first data; and the model validating circuit is configured to revalidate, subsequent to the retraining, all of the models including the reconfigured model using the second data.

In other features, the system further includes an anomaly detection circuit configured to detect an anomaly in one of the models failing validation. The model generating circuit is configured to generate a new model to replace the one of the models. The prediction circuit is configured to generate a portion of the predictions using the new model.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Figure 1:
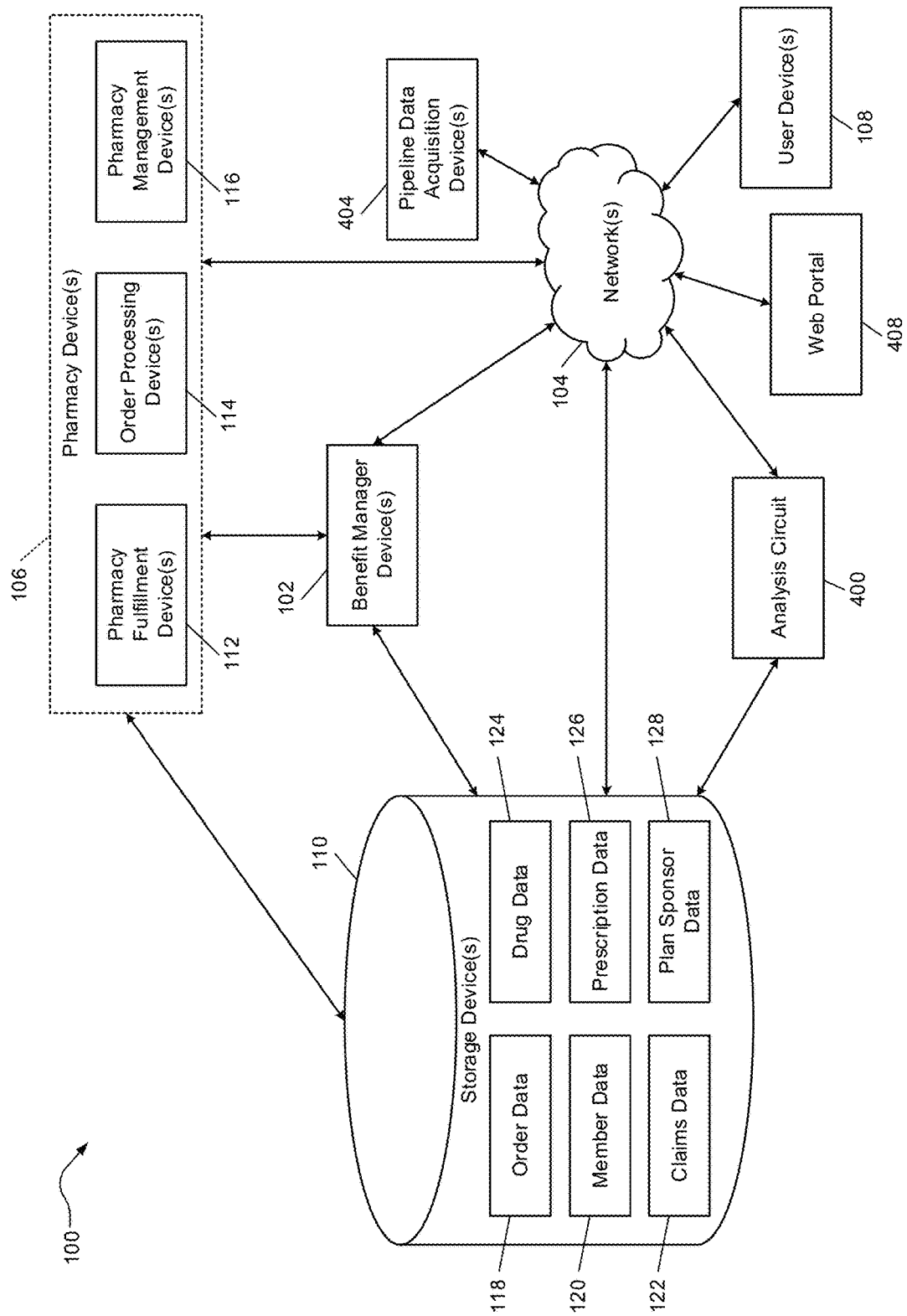
FIG. 1 is a functional block diagram of an example system including a high-volume pharmacy.

Throughout the present disclosure, the term "client" is broadly used to mean an entity that can use the model-based prediction system and method of the present disclosure. For example, the entity can include pharmacy benefit managers (PBMs), pharmaceutical companies (i.e., drug manufacturers or drug companies), health plans, government agencies, nonprofit organizations, mail-order pharmacies, and retail pharmacy stores. Accordingly, while the disclosure sometimes describes a PBM operating the system for the benefit of health plan clients, this is only one example of the disclosure's applicability.

The present disclosure describes a model-based system and method for predicting drug trend data and patient spending or a client. While patient spending can be measured using a number of different metrics, the example metric used in this disclosure is per member per month (PMPM) spending. Depending on the client, this metric may use a different timeframe, such as per fortnight or per 6-month period. Further, the metric may use another unit than per member (for example, per household or per family).

As explained below in detail with reference to FIGS. 4A-8B, historical data of the client is analyzed to generate, train, and validate various prediction models. These models are then used to provide predictions to the client regarding its drug trend and PMPM spending for a time period in the future based on past performance data of the client. The predictions can be provided to the client in the form of various easy-to-understand graphical representations (e.g., graphs, charts, tables, reports, and so on) as well as optionally in the form of downloadable raw data for use or rendering by the client. For example, the raw data may be provided in the form of XML (extensible markup language), CSV (comma-separated value), or JSON (JavaScript Object Notation).

Briefly, each model provides a directionally accurate forecast of drug trend and PMPM spending to the client using predictive analytical techniques. A model is a time-series model that forecasts future drug trend and PMPM values using one or more of machine learning, pattern recognition, and regression, each of which is briefly explained below.

Machine learning is a field of data analysis that combines statistical methods and computer science to construct sophisticated algorithms for exploiting trends and behaviors from large data sets. The algorithms are sets of rules for identifying important drivers of drug spending, their transformations (e.g., taking a metric and converting it to a ratio), and capturing non-linear relationships and stress-testing discovered links on new data. The new data is typically withheld from the algorithm training and reserved solely for testing as explained below in detail.

Pattern recognition encompasses characterization and recognition of systematic patterns over time. Such patterns are classified into (1) trend/drift (e.g., upward, downward, or flat), (2) seasonality (e.g., utilization spikes in asthma, viral infections, and so on), (3) cyclicality (e.g., plan changes in the beginning of the year and mid-year), and (4) noise (i.e., small fluctuations in PMPM spending not associated with any of the model inputs).

Regression in this context establishes a quantifiable link between PMPM cost and its drivers (e.g., prior trend, patient demographics, drug mix, member incentives, mail order utilization, and so on) by making the difference between the forecast and actuals as small as possible.

All three techniques establish weights and direction between drug spending drivers and PMPM cost by allowing the algorithms to "learn" from historical data. Once appropriate rules are established, they are applied in the form of a model to the most recent timeframe and run a desired time period into the future (e.g., 12, 24, or 36 months) to calculate PMPM cost. The model estimates are further refined by accounting for anticipated market events (e.g., patent expirations, new brand drug launches, and so on) with details provided by pipeline data. As one example, pipeline data in the present disclosure includes data received from a PBM-developed resource, such as the Office of Clinical Evaluation & Policy (OCEP) at Express Scripts, Inc.

One of the many benefits of the model flows from its targeted nature of using client-specific historical data to account for a population's unique drug utilization and drug mix patterns. Relevant features (e.g., demographics, drug utilization, drug costs, member incentives, seasonal trends, and so on) are extracted from the historical data and are aligned with drug spending over time for selected traditional drug classes (e.g., top 20) and selected specialty drug classes (e.g., top 10). In various implementations, model reliability improves with at least six months of data, and improves even more with two years of data. In various implementations, model reliability improves when a client population has an average monthly membership of at least about 1500 members.

Thus, the model uses client-specific past performance and key client data to forecast future trends through pattern recognition in the historical data by using machine learning. The model uses drug pipeline assumptions regarding the scale of their impact on new drugs/therapies. The model can be adapted for known plan design changes and/or pricing changes. Further, the model can take into account known or anticipated variables about the client such as, for example, population shifts (e.g., when the client sells or acquires old/new business), future formulary changes that can shift the drug mix, copay structures, month and year of anticipated changes, and so on. The model forecast is an estimate generated based on client-specific experience and future drug pipeline.

For a quick roadmap of the present disclosure, the present disclosure is organized as follows. To fully understand various aspects of the present disclosure, workings of a high-volume pharmacy, including data gathering, interfacing between different parties or stakeholders, and fulfillment are described with reference to FIGS. 1-3. A broad overview of the model-based prediction system and method of the present disclosure is presented using block diagrams shown in FIGS. 4A-4B and flowcharts shown in FIGS. 5A-5B. A detailed description of the present disclosure is then provided with reference to FIGS. 6A-6C. Additional supporting details of model generation, training, and validation are further explained using FIGS. 7A-8B.

High-Volume Pharmacy

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, client, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other and with the benefit manager device 102 directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may also include health data about a member, such as conditions the member is diagnosed with, such as hypertension, high cholesterol, or diabetes. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
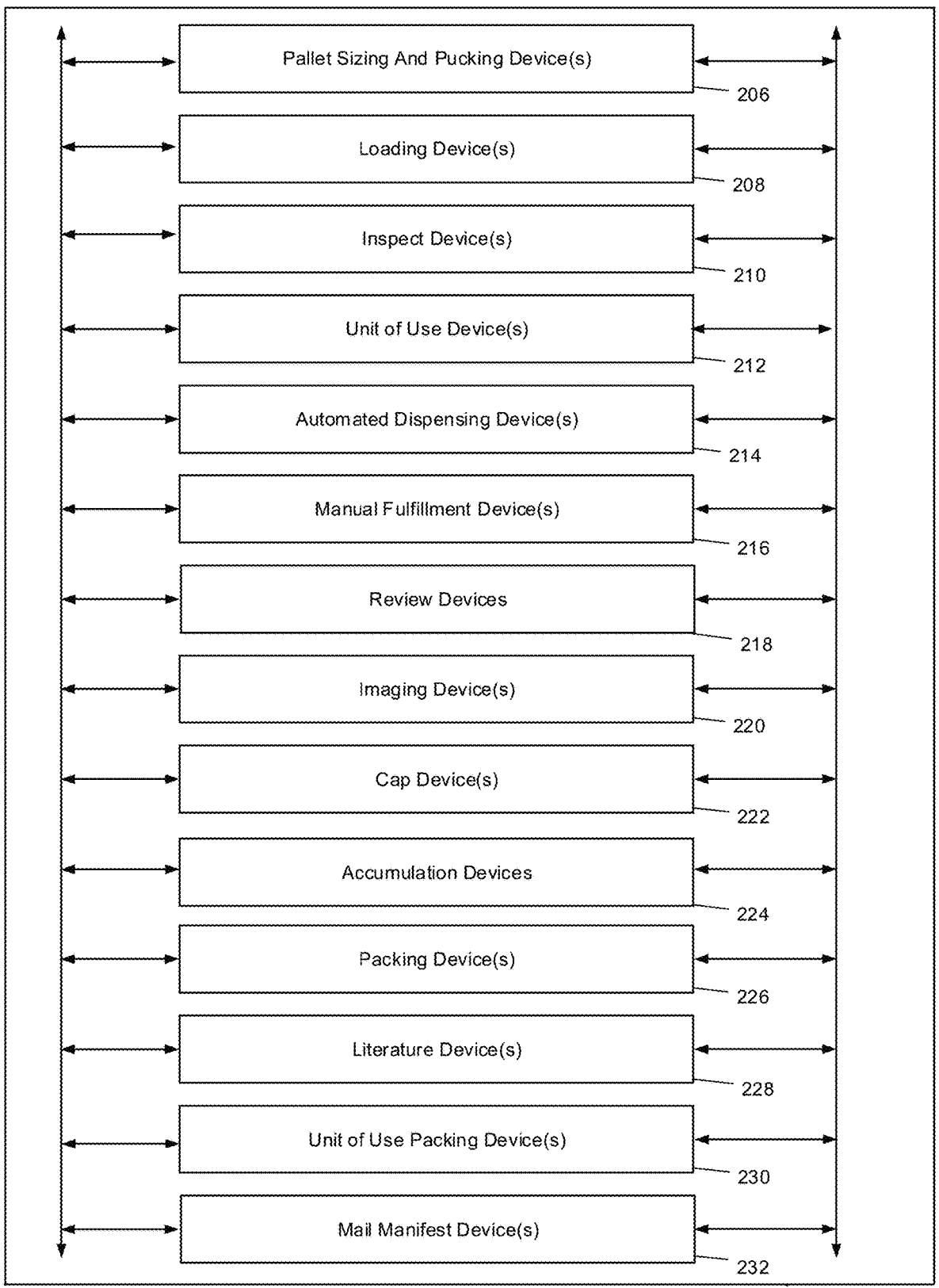
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container.

The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
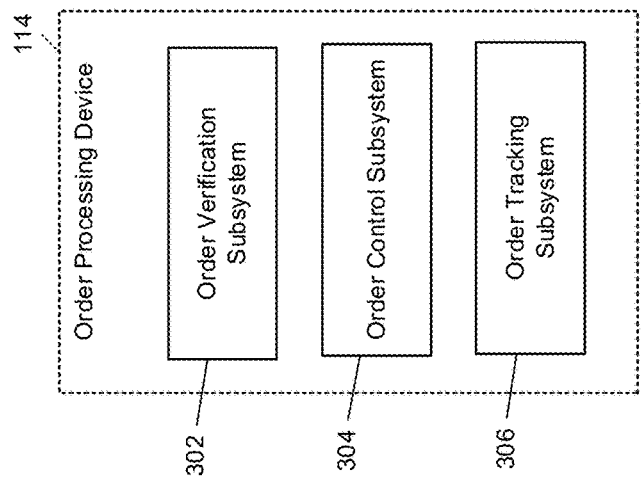
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be composed of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Model-Based Prediction System and Method

Referring back to FIG. 1, an analysis circuit 400 acquires historical data for a client (e.g., a plan benefit manager or PBM) from the storage devices 110. A pipeline data acquisition device 404 optionally acquires and processes data regarding drugs in a development, approval, and distribution pipeline and provides the pipeline data to the analysis circuit 400. For example, the pipeline data can include, but is not limited to, market events such as data regarding new drugs awaiting approval, new drugs being patented, drugs with expiring patents, generic drugs to be launched, and so on. The pipeline data can further include data about historical impact of such market events on prior predictions of drug trend and per member per month (PMPM) spending. The analysis circuit 400 analyzes the historical data of the client and may additionally analyze the pipeline data to generate, train, and validate models that provide predictions for drug trend and PMPM spending to the client. The analysis circuit 400 provides the predictions to the client, such as via a web portal 408.

Figure 4A:
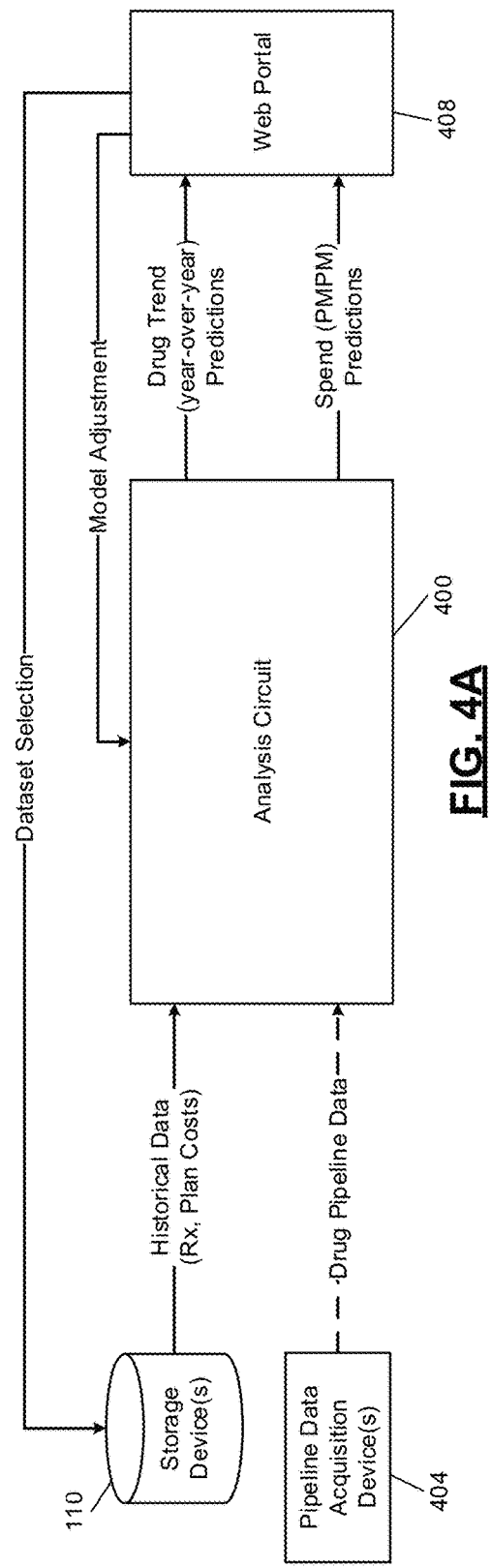
FIG. 4A is a functional block diagram of an example of a model-based prediction system according to the principles of the present disclosure.
Figure 4B:
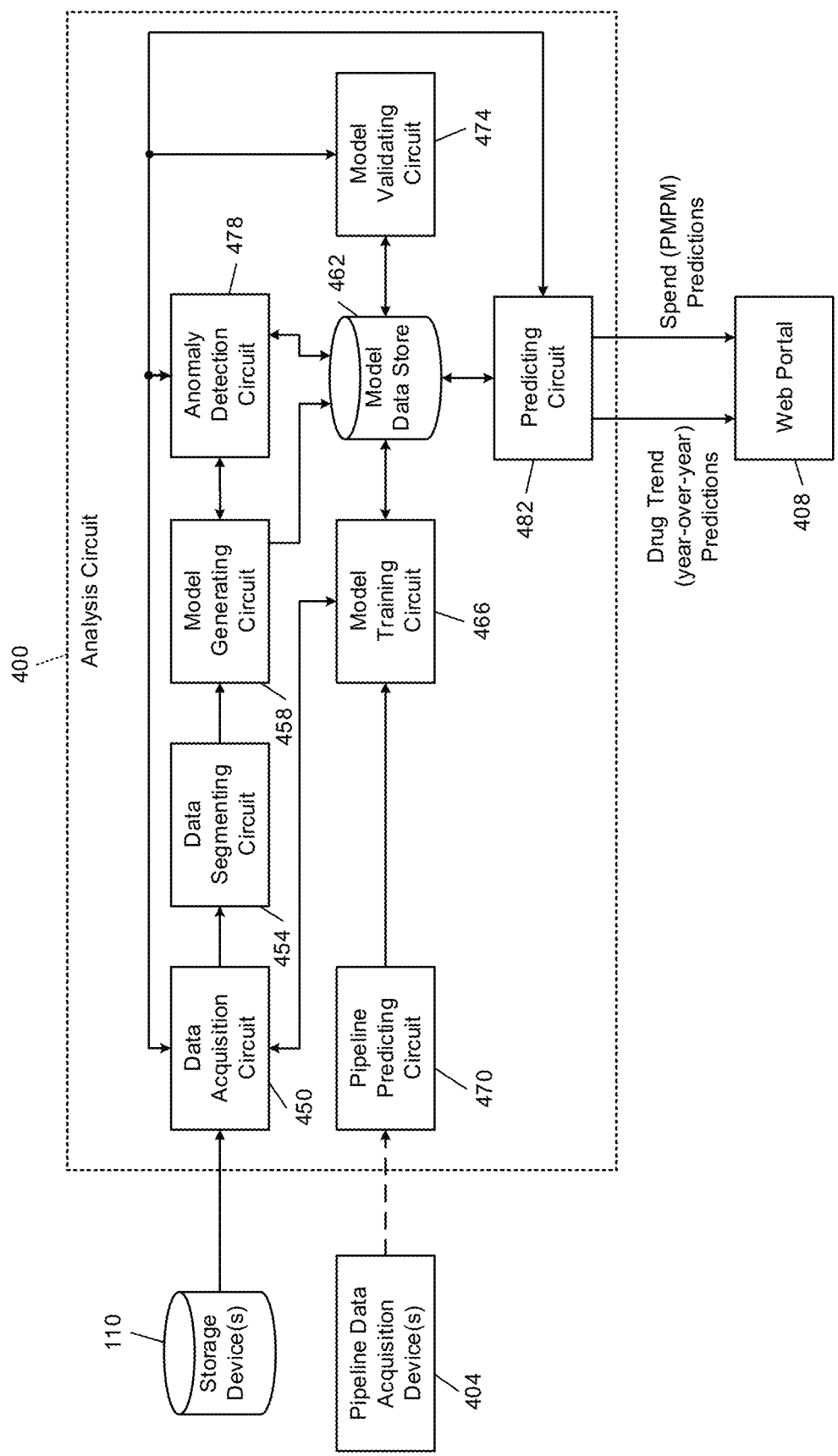
FIG. 4B is a functional block diagram of an example of an analysis circuit of the model-based prediction system of FIG. 4A according to the principles of the present disclosure.

FIGS. 4A and 4B show an example of an implementation of the analysis circuit 400. In FIG. 4A, the analysis circuit 400 can select a client's historical data from the data stored in the storage devices 110. The analysis circuit 400 can optionally also use data provided by the pipeline data acquisition device 404 regarding market events such as drugs in the pipeline and any historical impact of such market events on drug trends and PMPM spending. The client can use the web portal 408 to interact with the analysis circuit 400 to observe underlying data and inputs to the analysis circuit 400.

The analysis circuit 400 analyses one or more of these data to generate, train, and validate models to predict the drug trend and PMPM spending of the client. The analysis circuit 400 can present (e.g., display) the drug trend and PMPM spending predictions to the client on the web portal 408 in the form of graphical representations. In various implementations, the client may be able to download raw data from the web portal 408 or via another mechanism such as a web-enabled application programming interface (API). Further, the client can also use the web portal 408 to adjust the models when necessary as explained below.

In FIG. 4B, an example of a simplified functional block diagram of the analysis circuit 400 is shown. In this example, the analysis circuit 400 includes a data acquisition circuit 450, a data segmenting circuit 454, a model generating circuit 458, a model data store 462, a model training circuit 466, a pipeline predicting circuit 470, a model validating circuit 474, an anomaly detection circuit 478, and a predicting circuit 482. These circuits are initially described below briefly. These circuits are subsequently described in detail with reference to FIGS. 6A-6C.

Briefly, the data acquisition circuit 450 acquires a client's historical data such as prescription data, plan costs, historical drug spend data, and member population profile data from the storage devices 110. In various implementations, the client can use the web portal 408 to interact with the analysis circuit 400 (e.g., with the data segmenting circuit 454) to observe underlying data and inputs to the analysis circuit 400.

The data segmenting circuit 454 segments the acquired historical data according to therapy classes as explained below in detail with reference to FIGS. 6A-6C. The model generating circuit 458 analyzes the segmented data, learns patterns, and generates a model for each therapy class. The model data store 462 stores the models generated by the model generating circuit 458.

The model training circuit 466 trains the models using the X months of client data that is older than the client's most recent Y months of data. For example, if the client's past 24 months of data is available, the model training circuit 466 trains the models using the client's data that is 7-24 months old. The client's most recent 6 months' data is reserved for validating trained models.

The pipeline predicting circuit 470 receives the pipeline data regarding market events from the pipeline data acquisition device 404. Based on the pipeline data, the pipeline predicting circuit 470 predicts the impact that the market events (e.g., patent expirations, generic drug launches, and so on) may have on the drug trend and PMPM spending predictions being generated for the client. The model training circuit 466 trains the models by taking into account the predicted impact of the market events. The trained models are stored in the model data store 462.

The model validating circuit 474 validates the trained models and stores the validated models in the model data store 462. If a model fails to validate, the model inputs are reconfigured. For example, some features may be simplified from the data acquired by the data acquisition circuit 450. The client can also reconfigure the models using the web portal 408 by selecting different (for example, fewer) data sets with which to generate the models if one or more models fails to validate.

An anomaly detection circuit 478 detects an anomaly such as, for example, if a model consistently fails to validate. If an anomaly is detected, the model generating circuit 458 generates a new model (using, for example, forward-looking linear regression) that is stored in the model data store 462 and is directly used to provide predictions. After all the models are validated, and any anomalous model is replaced by a corresponding new model, the model training circuit 466 trains all the validated and optionally the new models using all of the client's data (e.g., all of the X+Y months' data mentioned above). The model training circuit 466 stores the trained validated models in the model data store 462.

Using the trained validated models and any of the new models, the predicting circuit 482 generates the drug trend and PMPM spending predictions for the client for future P months (e.g., future 12, 24, or 36 months) based on the client's past data (e.g., at least the past 12 months' data). The predictions can be graphically displayed on the web portal 408 or can be made available as raw tabular data for the client to download and use as it desires.

Figures 5A, 5B:
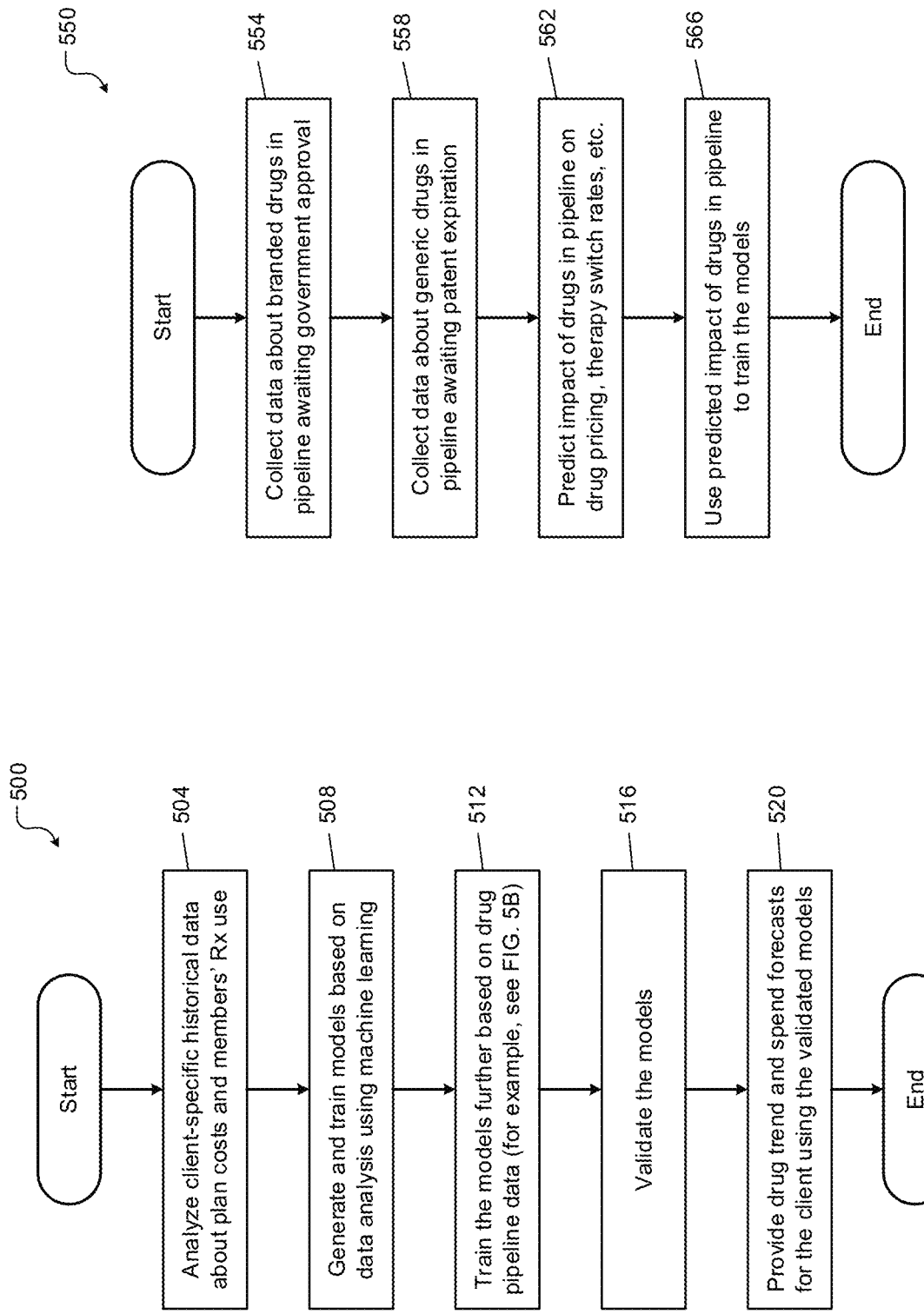
FIGS. 5A and 5B are flowcharts showing an overview of an example of a model-based prediction method according to the principles of the present disclosure.

FIGS. 5A and 5B show examples of methods for generating drug trend and PMPM spending predictions for a client. These figures show an overview of the method. A more detailed flowchart is shown and subsequently described below with reference to FIGS. 6A-6C.

In FIG. 5A, a method 500 for generating drug trend and PMPM spending predictions for a client is generally shown. For example, the method 500 is performed by the analysis circuit 400 of FIGS. 1, 4A, and 4B. At 504, control analyzes client-specific historical data (e.g., plan costs, members' prescription use, and so on). At 508, control generates and trains models for various therapy classes based on the analyzed data using machine learning techniques. At 512, control optionally further trains models based on drug pipeline data. At 516, control validates the trained models. At 520, control provides drug trend and PMPM spend predictions for the client using the validated models.

In FIG. 5B, a method 550 for further training the models based on drug pipeline data is shown. At 554, control collects data about brand-name drugs in pipeline awaiting government approval. At 558, control collects data about generic drugs in pipeline awaiting patent expiration. At 562, control predicts impact of drugs in pipeline (both brand-name and generic) on drug pricing, new diagnoses rates, therapy switch rates, and so on. At 566, control uses the predicted impact of drugs in pipeline to train the models.

Figure 6A:
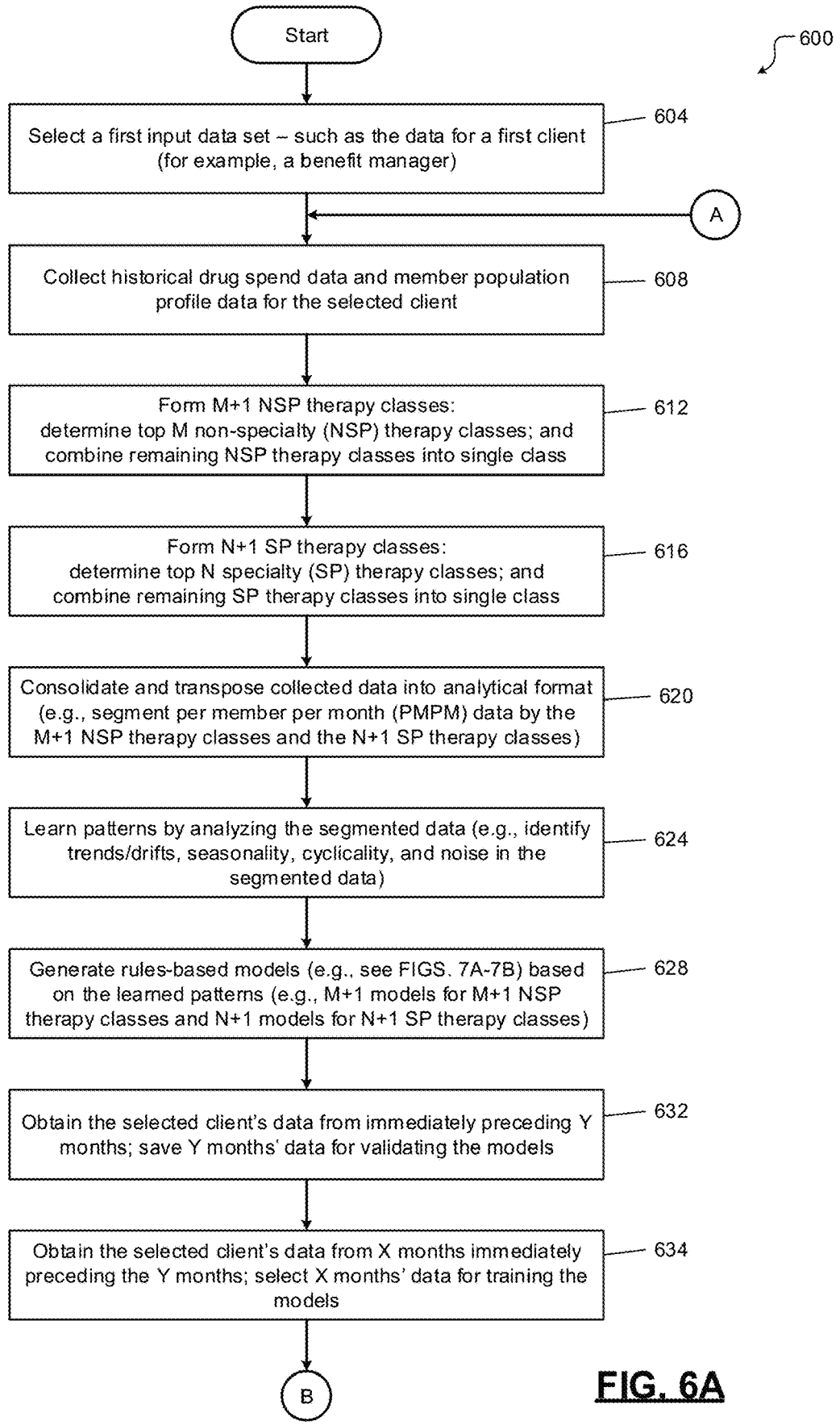
FIGS. 6A, 6B, and 6C are flowcharts showing details of the model-based prediction method of FIGS. 5A and 5B according to the principles of the present disclosure.
Figure 6B:
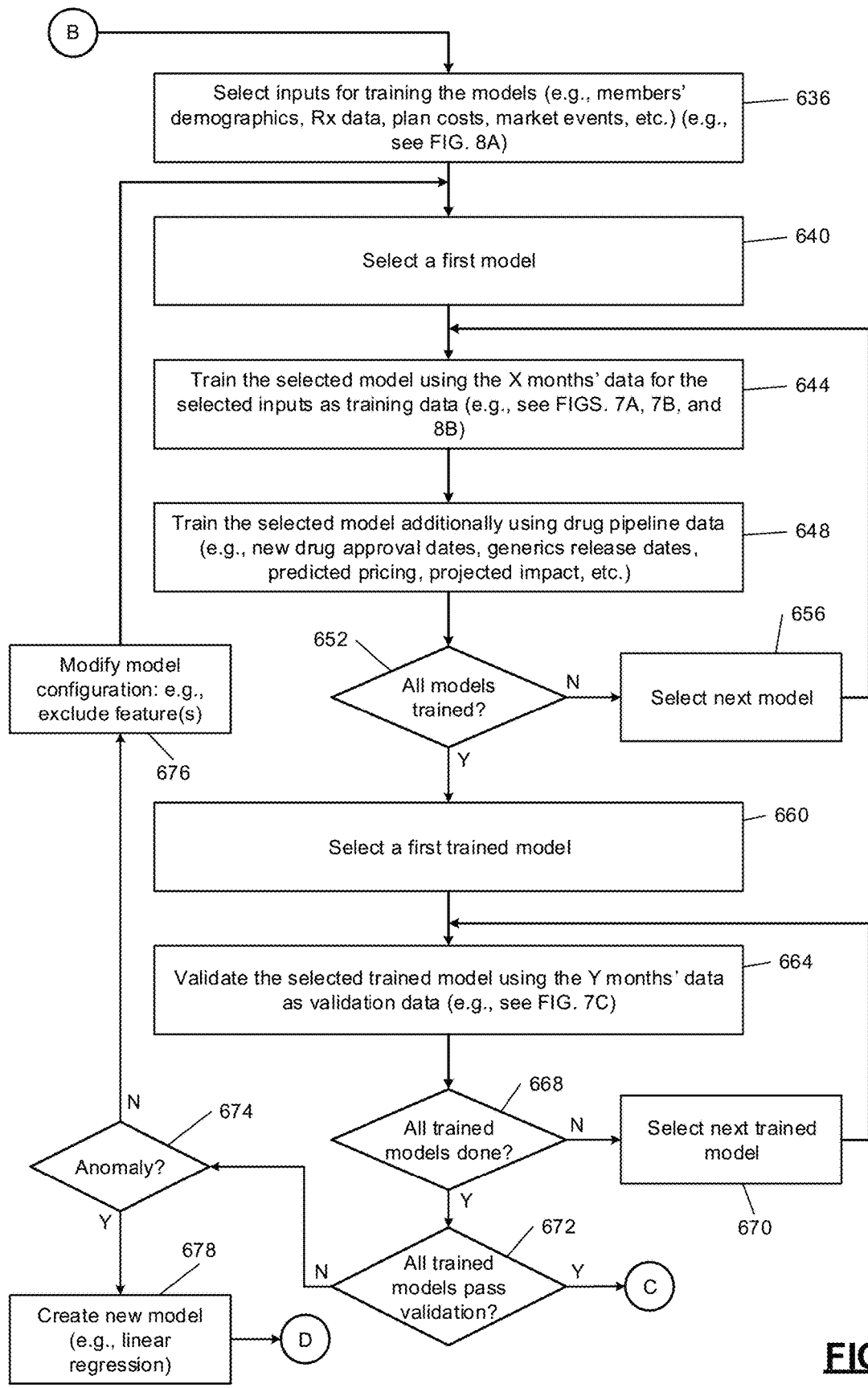
Figure 6C:
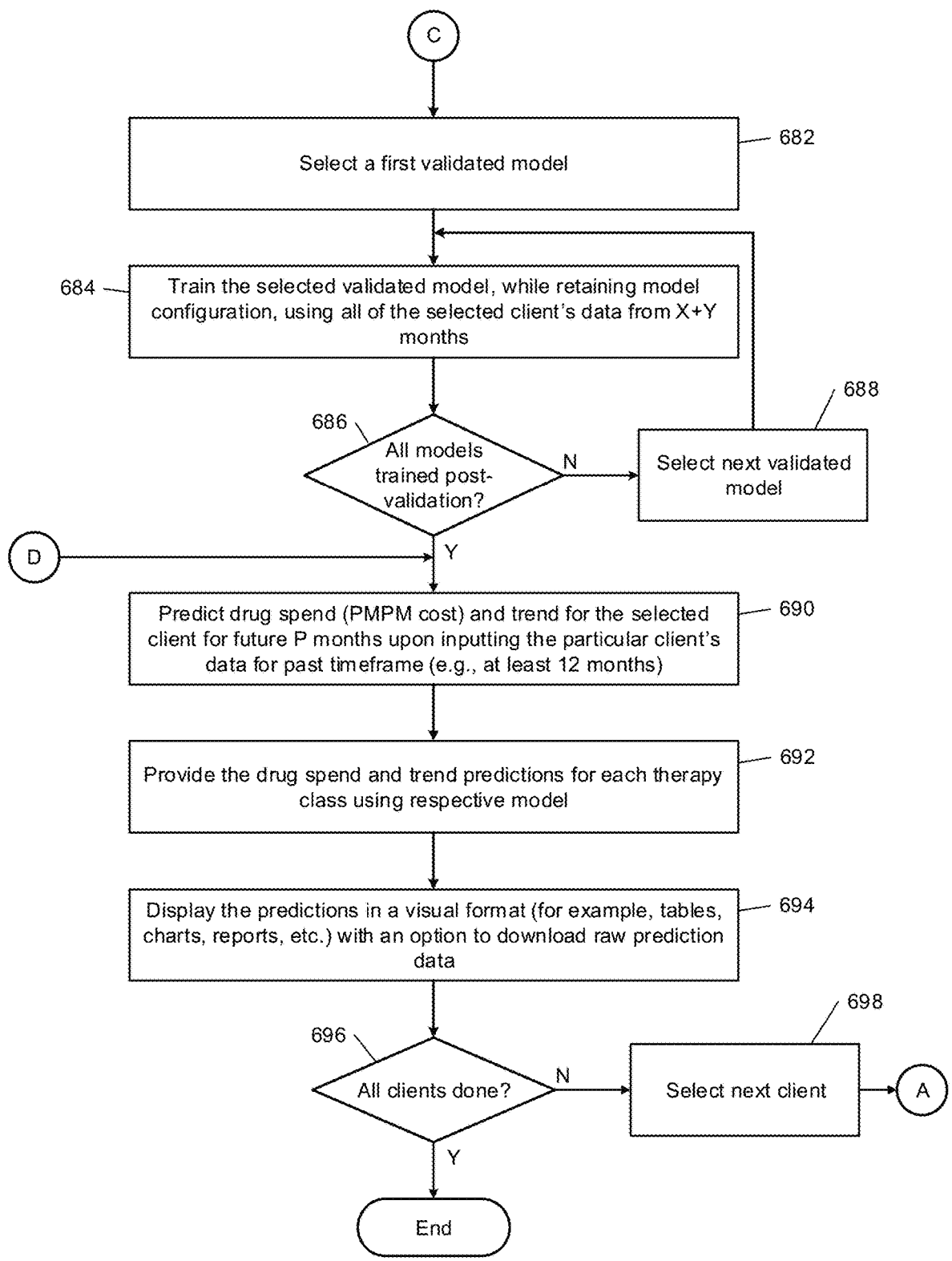

FIGS. 6A-6C together show an example of a method 600 for generating drug trend and PMPM spending predictions for clients. For example, the method 600 may be performed by the analysis circuit 400 of FIGS. 1, 4A, and 4B. At 604, control selects a first input data set such as the data of a first client (e.g., a plan benefit manager or PBM). Alternatively, the first input data set can be for any other entity such as a drug manufacturer, a pharmacy, and so on. For example, the data acquisition circuit 450 of FIG. 4B can select the first input data set from the data stored in the storage devices 110.

At 608, control collects historical drug spend data, member population profile data, and so on for the selected client. For example, the data acquisition circuit 450 of FIG. 4B can collect the historical data for the selected client from the data stored in the storage devices 110. For example, the historical data may be for a period of the prior 2 to 3 years. In some instances, the period may be shorter or longer than 2 to 3 years. In various implementations, at least one year of data is preferred to provide reliable predictions.

For many reasons, selecting and collecting proper historical data can be important for generating reliable predictions for clients. For example, the historical data may include seasonal fluctuations in prescriptions that may be caused by events such as, for example, changes in season, beginning of a school year, and so on. The seasonal fluctuations in prescriptions can also be due to seasonal allergies, flu seasons, and so on. In other examples, the historical data may include fluctuations in plan expenditures at the beginning of a calendar year relative to the end of the calendar year depending on depletion levels of members' deductibles.

The historical data may vary from client to client due to various reasons including differences in plan designs, differences in demographics of member populations, and so on. For example, copays, deductibles, and so on may differ from plan to plan. Further, members employed for physical work (e.g., construction work) may have very different healthcare needs and claims compared to members employed to doing sedentary work (e.g., clerical work).

For example, members doing physical work may suffer predominantly from physical ailments such as back injuries, while members doing sedentary work may suffer from diseases such as obesity. In other examples, members employed in industrial and chemical manufacturing work may have very different healthcare needs and claims. For example, members doing industrial manufacturing work (e.g., working on assembly lines in factories) may suffer from accident-related or repetitive-stress-related injuries while members handling chemicals (e.g., working in refineries, mines, and so on) may suffer from chemical burns, chemical exposure, skin and lung diseases, and so on.

Accordingly, different historical data can lead to different predictions for different clients. Therefore, selecting and collecting proper historical data sets can be important for generating reliable predictions for clients. Algorithms for generating predictions for different clients are uniquely tied to the clients' cost and utilization patterns, which are learned from the clients' respective historical data as follows.

Each client will have its own blueprint of top therapy classes categorized based on the amount of drug spending. Some examples of therapy classes can include diabetes, mental health, asthma, heart disease, birth control, and so on. Therapy classes can generally be of two types: non-specialty (NSP) therapy classes and specialty (SP) therapy classes. Notably, even if several clients have the same top therapy classes, their therapy model configurations are likely to be different and unique. For example, one client's model for managing diabetes may be different from another client's model for managing diabetes.

At 612, control determines the top M non-specialty (NSP) therapy classes and combines (or, "lumps") any remaining NSP therapy classes into one additional NSP therapy class. In other words, control determines the top M+1 NSP therapy classes. At 614, control determines the top N specialty (SP) therapy classes and combines any remaining SP therapy classes into one additional SP therapy class. In other words, control determines the top N+1 SP therapy classes. Note that M and N are positive integers.

At 620, control consolidates and transposes the collected historical data into analytical format. For example, control segments per member per month (PMPM) data by the M+1 NSP therapy classes and the N+1 SP therapy classes. For example, the data segmenting circuit 454 of FIG. 4B segments the PMPM data by the M+1 NSP therapy classes and the N+1 SP therapy classes.

At 624, control learns patterns by analyzing the segment the data. For example, control identifies trends/drifts, seasonality, cyclicality, and noise in the segment the data. For example, the model generating circuit 458 of FIG. 4B learns the patterns by analyzing the segmented data.

At 628, control generates rules-based models (e.g., machine learning algorithms) based on the learned patterns. For example, control generates M+1 models for the M+1 NSP therapy classes and N+1 models for the N+1 SP therapy classes. For example, the model generating circuit 458 of FIG. 4B generates the rules-based models based on the learned patterns. The model generating circuit 458 stores the models in the model data store 462 of FIG. 4B. Further details of generating the models are shown and described below with reference to FIGS. 7A and 7B.

At 632, control obtains the selected client's data from immediately preceding Y months and saves the Y months of data for validating the models after the models are trained. For example, the Y months of data may be data from the past 6 months. Alternatively, the Y months data of may be for more or fewer months than 6. At 634, control obtains the selected client's data from X months immediately preceding the Y months and selects the X months of data for training the models before validating the models. For example, the X months of data may be from the 18-month period immediately before the most recent 6-month period. The X months of data may be for more or fewer months than 18.

At 632 and 634, for example, control may obtain a total of past X+Y months' data for the client (as numerical examples, X may be 18, and Y may be 6); save the immediately preceding Y months' data for validating the models; and use the X months' data that immediately precedes the Y months' data for training the models. For example, the model training circuit 466 of FIG. 4B obtains the selected client's past X+Y months' data and stores it in the model data store 462 of FIG. 4B.

Figure 8A:
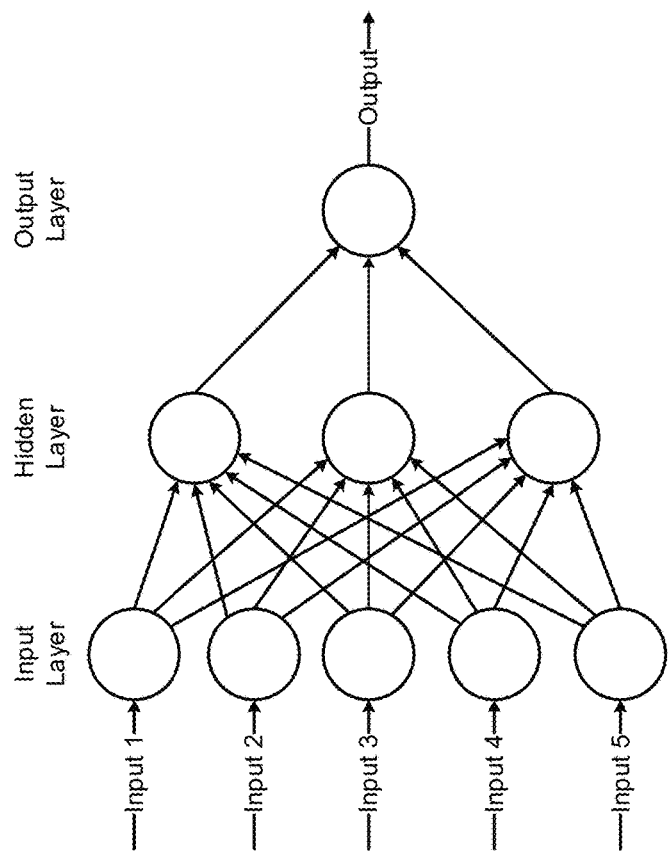
FIGS. 8A and 8B are graphical representations of example recurrent neural networks used to generate the models referenced in FIGS. 4A-6C.

At 636, control selects or configures the inputs for training the models. For example, the inputs may include plan members' demographics data, prescription data, plan costs, market events, and so on. For example, the model generating circuit 458 of FIG. 4B may select these inputs. FIG. 8A shows an example of a neural network with configurable inputs.

At 640, control selects a first model to train. For example, the model training circuit 466 of FIG. 4B may select a first model from the model data store 462 to train. At 644, control trains the selected model using the X months' data for the selected inputs as training data. For example, the model training circuit 466 of FIG. 4B may train the selected model using the X months' data for the selected inputs as training data. The model training circuit 466 stores the trained model in the model data store 462 of FIG. 4B. Further details of training the models are shown and described below with reference to FIGS. 7A and 7B. FIG. 8B shows an example of weights for nodes of a neural network that can be optimized during training using machine learning techniques.

At 648, control optionally trains the selected model additionally using drug pipeline data (e.g., new drug approval dates, generic drug release dates, predicted pricing of the new drugs, projected impact of the new drugs, and so on). For example, the pipeline predicting circuit 470 of FIG. 4B provides the drug pipeline data to the model training circuit 466, which trains the selected model additionally using the drug pipeline data. The model training circuit 466 stores the trained model in the model data store 462 of FIG. 4B.

At 652, control determines whether all models are trained. At 656, if some of the models still remain to be trained, control selects the next model and returns to 644. For example, the model training circuit 466 of FIG. 4B determines whether all the models are trained and selects the next model from the model data store 462 of FIG. 4B for training if some of the models remain to be trained.

At 660, if all the models are trained, control selects a first trained model for validation. For example, the model validating circuit 474 of FIG. 4B selects a first trained model from the model data store 462 of FIG. 4B for validation. At 664, control validates the selected trained model using the Y months' data as validation data. For example, the model validating circuit 474 validates the selected trained model using the Y months' data from the model data store 462 of FIG. 4B as validation data. The model validating circuit 474 stores the validated model in the model data store 462. Further details of validating the trained models are shown and described below with reference to FIG. 7C.

At 668, control determines whether all the trained models are validated. At 670, if some of the trained models still remain to be validated, control selects the next trained model and returns to 664. For example, the model validating circuit 474 of FIG. 4B determines whether all the trained models are validated and selects the next trained model from the model data store 462 of FIG. 4B for validating if some of the trained models remain to be validated.

At 672, control determines whether all of the trained models passed validation. At 674, if one of the trained models did not pass validation, control determines if there is an anomaly due to which the trained model did not pass validation. At 676, if control determines that there is no anomaly, control modifies the configuration of the model that failed validation for reasons other than an anomaly, and control returns to 640.

Accordingly, if all the trained models do not pass validation, and if there is no anomaly, all the models are retrained and revalidated after the model failing validation is reconfigured. In some implementations, however, if all the trained models do not pass validation, and if there is no anomaly, all the models are not retrained and revalidated after the model failing validation is reconfigured. Instead, only the models that do not pass validation (and where an anomaly is not the cause of their failure) are reconfigured, re-rained, and revalidated.

At 674, if control determines that a trained model failed to validate due to an anomaly, control transfers to 678 and generates a new model (e.g., linear regression). The new model is not trained and not validated. The new model replaces the failed model in the model data store 462 of FIG. 4B. The new model is used to directly provide predictions as described at 690-694 below. For example, the anomaly detection circuit 478 of FIG. 4B performs anomaly detection, and the model generating circuit 458 generates the new model on detecting an anomaly.

At 682, all of the trained models without an anomaly passed validation, and so control selects a first validated model for further training on all of the data (i.e., the total data of X+Y months used earlier for training and validation). At 684, control trains the first validated model on all of the data. For example, the model training circuit 466 of FIG. 4B trains the first validated model from the model data store 462 of FIG. 4B and stores the trained validated model in the model data store 462. Notably, the configuration of the first validated model is retained and remains unchanged during the further training on all of the data.

At 686, control determines whether all the validated models have been trained on all the data (i.e., X+Y months' data). At 688, if some of the validated models still remain to be trained on all the data, control selects the next validated model and returns to 684. For example, the model training circuit 466 of FIG. 4B determines whether all the validated models are trained and selects the next validated model from the model data store 462 of FIG. 4B for training on all the data if some of the validated models remain to be trained on all the data.

At 690, after all the validated models are trained on all of the data (i.e., X+Y months' data), using the trained validated models, control generates predictions for the respective therapy classes for the selected client. A trained validated model for a therapy class predicts drug trend and PMPM spending for the therapy class. The drug trend predictions are further categorized for brand name drugs and generic drugs for each of the therapeutic classes. Each trained validated model generates the predictions for future P months' period (e.g., 12, 24, or 36 months, or any number of months) based on the selected client's past performance data (e.g., preferably at least past 12 months, to reliably account for yearly, seasonal, and cyclical data). At 692, control provides these predictions for each therapy class using a respective trained validated model. For example, the predicting circuit 482 of FIG. 4B generates these predictions and provides these predictions to the web portal 408 of FIGS. 1, 4A, and 4B.

At 694, control displays these predictions in a visual format (e.g., in the form of graphs, charts, tables, reports, and so on). For example, the predicting circuit 482 of FIG. 4B displays these predictions on the web portal 408 of FIGS. 1, 4A, and 4B. Control also provides an option for the client to download these predictions in a raw format (i.e., in an unformatted form). The client can use the raw predictions data in a manner that the client desires (e.g., to generate visual displays to present the predictions; to augment an internal database for further research, quality control, sales, marketing; and so on).

At 696, control determines if another client requests predictions. At 698, if another client requests predictions, control selects the other client as described at 604, and control returns to 608. Otherwise, control ends.

Figure 7C:
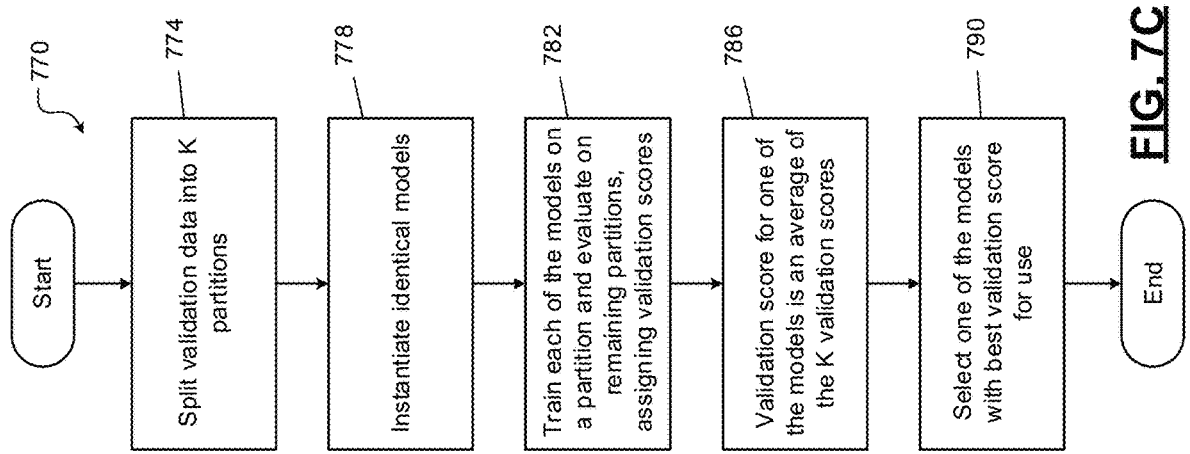
FIGS. 7A, 7B, and 7C are flowcharts showing examples of methods for generating, training, and validating models referenced in FIGS. 4A-6C.
Figure 7B:
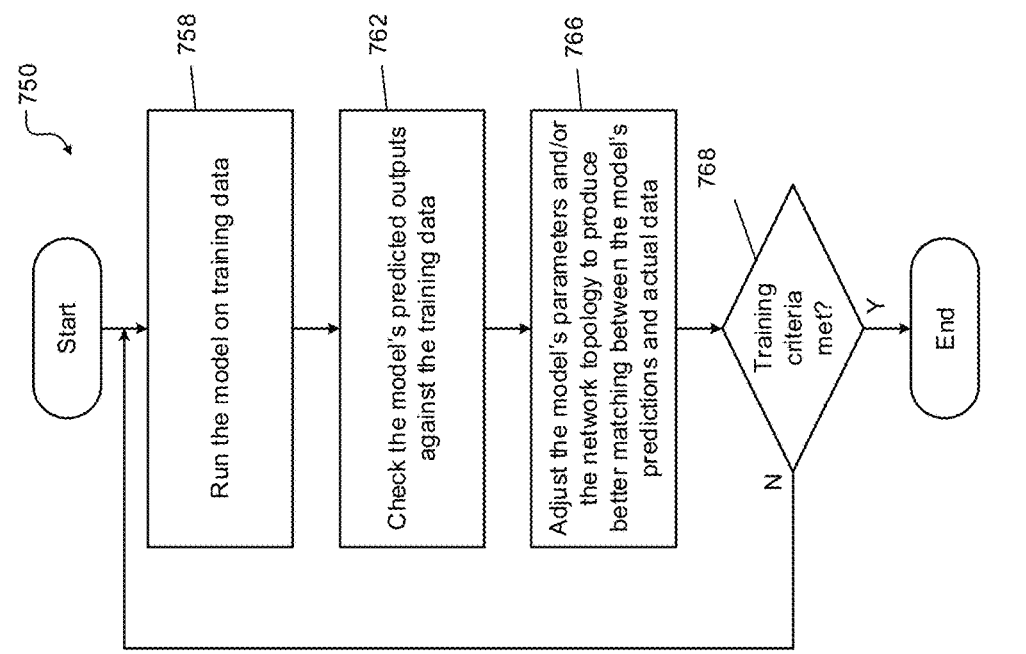
Figure 7A:
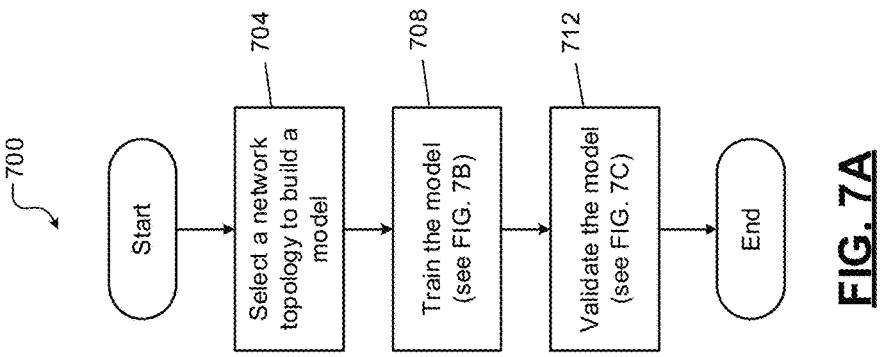
Figure 8B:
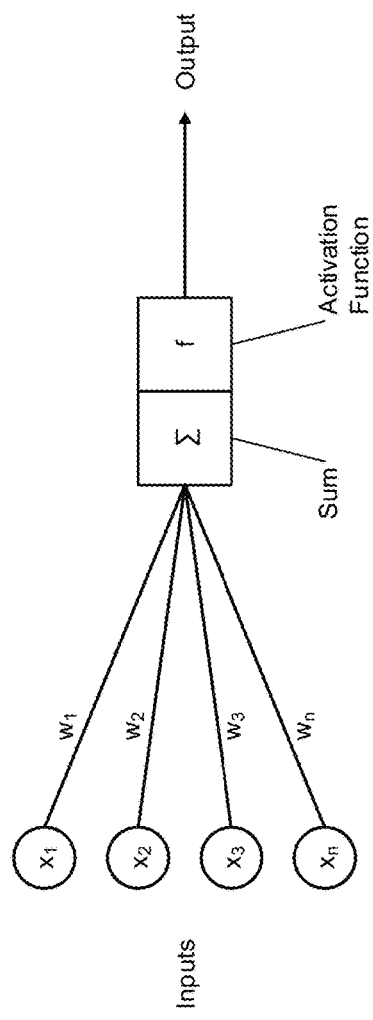

FIGS. 7A-7C show examples of methods for generating, training, and validating models such as those described with reference to FIGS. 4A-6C above. FIG. 7A shows a method 700 for generating a model. For example, the model generating circuit 458, the model training circuit 466, and the model validating circuit 474 of FIG. 4B perform the method 700.

At 704, control selects a network topology to define and build a model. For example, control may define the model by selecting a network topology for a recurrent neural network. An example of a recurrent neural network is shown in FIG. 8A. For example, selecting a network topology includes selecting number of inputs, number of neurons, and number of layers of the recurrent neural network. FIGS. 8A and 8B and corresponding description below explain model generation in further detail. For example, the model generating circuit 458 defines and builds the model as described above and as shown in FIGS. 8A and 8B.

At 708, control trains the model. FIG. 7B and corresponding description below explain model training in further detail. For example, the model training circuit 466 of FIG. 4B may train the model as described below. At 712, control validates the model. FIG. 7C and corresponding description below explain model validation in further detail. For example, the model validating circuit 474 of FIG. 4B may validate the model as described below.

FIG. 7B shows a method 750 for training a model. For example, the model training circuit 466 of FIG. 4B may use the method 750 to train the models described above. At 758, control runs the model on training data (e.g., X months' data described above). At 762, control checks the outputs predicted by the model against the training data. At 766, control adjusts the model's parameters (e.g., configuration of the model inputs explained above) and/or the network technology to produce better matching between the model's predictions and the actual data. At 768, control determines whether the model meets some predetermined training criteria. Control returns to the 758 if the model does not meet the predetermined training criteria. Control ends if the model meets the predetermined training criteria.

FIG. 7C shows a method 770 for validating a model. For example, the model validating circuit 474 of FIG. 4B may use the method 770 to validate the models described above. The method 770 is called a K-fold validation method and is shown as an example only. There are other methods of validating models that may be employed instead to validate the various models described above with reference to FIGS. 4A-6C.

At 774, control splits the data used for validation (e.g., Y months' data) into K partitions, where K is an integer greater than one. At 778, control instantiates plural identical models. At 782, for each instantiated model, control trains a model on one partition and evaluates the model on the remaining partitions. Control assigns validation scores for each evaluation. At 786, control determines an average of K validation scores of a model as the validation score for the model. At 790, control selects one of the models with the highest validation score for use.

Other validation methods can be used to validate the models. For example, an N-fold cross-validation method may be used. In this method, a dataset is divided into one final test set and N other subsets, where N is an integer greater than one. Each model is trained on all but one of the subsets to get N different estimates of a validation error rate. The model with the lowest validation error rate is selected for use.

FIGS. 8A and 8B show an example of a recurrent neural network used to generate models such as those described above with reference to FIGS. 4A-6C using machine learning techniques. Machine learning is a method used to devise complex models and algorithms that lend themselves to prediction (e.g., drug trend and PMPM spending predictions). The models generated using machine learning such as those described above with reference to FIGS. 4A-6C can produce reliable, repeatable decisions and results, and uncover hidden insights through learning from historical relationships and trends in the data.

The purpose of using the recurrent-neural-network-based model and training the model using machine learning as described above with reference to FIGS. 4A-7B is to directly predict dependent variables without casting relationships between the variables into mathematical form. The neural network model includes a large number of virtual neurons operating in parallel and arranged in layers. The first layer is the input layer and receives raw input data. Each successive layer modifies outputs from a preceding layer and sends them to a next layer. The last layer is the output layer and produces output of the system.

FIG. 8A shows a fully connected neural network, where each neuron in a given layer is connected to each neuron in a next layer. In the input layer, each input node is associated with a numerical value, which can be any real number. In each layer, each connection that departs from an input node has a weight associated with it, which can also be any real number (see FIG. 8B). In the input layer, the number of neurons equals number of features (columns) in a dataset. The output layer can have multiple continuous outputs.

The layers between the input and output layers are hidden layers. The number of hidden layers can be one or more (one hidden layer may be sufficient for most applications). A neural network with no hidden layers can represent linear separable functions or decisions. A neural network with one hidden layer can perform continuous mapping from one finite space to another. A neural network with two hidden layer can approximate any smooth mapping to any accuracy.

The number of neurons can be optimized. At the beginning of training, a network configuration is more likely to have excess nodes. Some of the nodes may be removed from the network during training that would not noticeably affect network performance. For example, nodes with weights approaching zero after training can be removed (this process is called pruning). The number of neurons can cause underfitting (inability to adequately capture signals in dataset) or over-fitting (insufficient information to train all neurons; network performs well on training dataset but not on test dataset).

Various methods and criteria can be used to measure performance of a model. For example, root mean squared error (RMSE) measures the average distance between observed values and model predictions. Coefficient of Determination ($R^2$) measures correlation (not accuracy) between observed and predicted outcomes. This method may not be reliable if the data has a large variance. Other performance measures include irreducible noise, model bias, and model variance. A high model bias for a model indicates that the model is not able to capture true relationship between predictors and the outcome. Model variance can indicate whether a model is not stable (a slight perturbation in the data will significantly change the model fit).

The analysis circuit 400 of FIGS. 1, 4A, and 4B in general, and the model generation circuit 458 and the model training circuit 366 in particular, take into account the design and performance criteria described above with reference to FIGS. 8A-8B when generating and training the models described above with reference to FIGS. 4A-6C.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP:

Hypertext Preprocessor), Scala, Eiffel, Smalltalk, Erlang, Ruby, Flash®, Visual Basic®, Lua, MATLAB, SIMULINK, and Python®.

What is claimed is:

1. A method comprising:
receiving historical data collected from a client, wherein the client is associated with a plurality of members, and wherein the historical data includes per member metrics for the client and demographic information for the plurality of members;
identifying a set of therapeutic classes for the client based on the per member metrics and the demographic information;
segmenting the historical data into a respective data set for each therapeutic class, wherein the respective data set for the respective therapeutic class includes per member metrics corresponding to the respective therapeutic class;
for each therapeutic class of the set of therapeutic classes:
    determining a pattern for the per member metrics corresponding to the respective therapeutic class;
    generating a respective predictive model based on the pattern, wherein the respective predictive model is configured to generate, as output for the respective therapeutic class, a per member metric prediction for an input period of future time; and
    training a neural network of the respective predictive model using a two-stage training process, wherein a first stage of the two-stage training process trains the respective predictive model with the historical data collected from the client, and wherein a second stage of the two-stage training process trains the respective predictive model with drug market event data; and
generating predictions for the set of therapeutic classes by using the predictive models of each therapeutic class.

2. The method of claim 1 wherein the training of the neural network includes:
obtaining the drug market event data and historical market data characterizing an impact of the historical drug market event data on per member metrics;
determining a predicted impact for the obtained drug market event data based on the historical market data;
generating training data for the second stage of the two-stage training process that includes the obtained drug market event data associated with the predicted impact; and
training the respective predictive model during the second stage of the two-stage training using the training data generated for the second stage training process.

3. The method of claim 2 wherein:
the drug market event data and the historical market data characterize an impact of the historical drug market event data on drug spending trends; and
for each therapeutic class, the respective predictive model is configured to generate, as output, a drug spending trend prediction for the input period of future time.

4. The method of claim 1 further comprising providing the predictions via a web portal in at least one of a displayable graphical format and a downloadable data structure.

5. The method of claim 4 wherein the web portal is configured to facilitate selection of a training data set for each respective predictive model.

6. The method of claim 1 wherein the per member metric corresponds to a specific length of time.

7. The method of claim 6 wherein the per member metric is based on total spending within the specific length of time.

8. The method of claim 1 wherein the predictions are further categorized for brand name, generic, and specialty drugs for each of the therapeutic classes.

9. The method of claim 1 wherein:
the method further comprises validating the trained models using first data collected over a first time period;
the historical data used to train the predictive models during the first stage corresponds to second data from a second time period; and
the first time period is shorter in duration and more recent than the second time period.

10. The method of claim 9 wherein the drug market event data includes data about new drugs to be released and about past impacts of release of other new drugs on year-over-year change in drug spending and on per member metrics.

11. The method of claim 9 further comprising:
training the validated models using the first data and the second data; and
generating the predictions using the trained validated models.

12. The method of claim 9 further comprising:
reconfiguring one of the predictive models in response to the one of the predictive models failing validation;
retraining all of the predictive models including the reconfigured model using the second data; and
revalidating, subsequent to the retraining, all of the predictive models including the reconfigured model using the first data.

13. The method of claim 9 further comprising:
generating a new predictive model to replace one of the predictive models in response to the one of the predictive models failing validation due to an anomaly; and
using the new predictive model to generate a portion of the predictions.

14. A non-transitory computer-readable medium comprising processor-executable instructions, the instructions including:
receiving historical data collected from a client, wherein the client is associated with a plurality of members, and wherein the historical data includes per member metrics for the client and demographic information for the plurality of members;
identifying a set of therapeutic classes for the client based on the per member metrics and the demographic information;
segmenting the historical data into a respective data set for each therapeutic class, wherein the respective data set for the respective therapeutic class includes per member metrics corresponding to the respective therapeutic class;
for each therapeutic class of the set of therapeutic classes:
    determining a pattern for the per member metrics corresponding to the respective therapeutic class;
    generating a respective predictive model based on the pattern, wherein the respective predictive model is configured to generate, as output for the respective therapeutic class, a per member metric prediction for an input period of future time; and
    training a neural network of the respective predictive model using a two-stage training process, wherein a first stage of the two-stage training process trains the respective predictive model with the historical data collected from the client, and wherein a second stage of the two-stage training process trains the respective predictive model with drug market event data; and
generating predictions for the set of therapeutic classes by using the predictive models of each therapeutic class.

15. The computer-readable medium of claim 14 wherein the training of the neural network includes:
- obtaining the drug market event data and historical market data characterizing an impact of the historical drug market event data on per member metrics;
- determining a predicted impact for the obtained drug market event data based on the historical market data;
- generating training data for the second stage of the two-stage training process that includes the obtained drug market event data associated with the predicted impact; and
- training the respective predictive model during the second stage of the two-stage training using the training data generated for the second stage training process.

16. The computer-readable medium of claim 15 wherein:
- the drug market event data and the historical market data characterize an impact of the historical drug market event data on drug spending trends; and
- for each therapeutic class, the respective predictive model is configured to generate, as output, a drug spending trend prediction for the input period of future time.

17. The computer-readable medium of claim 14 wherein the instructions include providing the predictions via a web portal in at least one of a displayable graphical format and a downloadable data structure.

18. The computer-readable medium of claim 14 wherein:
- the per member metric corresponds to a specific length of time; and
- the per member metric is based on total spending within the specific length of time.

19. The computer-readable medium of claim 14 wherein:
- the instructions further include validating the trained models using first data collected over a first time period;
- the historical data used to train the predictive models during the first stage corresponds to second data from a second time period; and
- the first time period is shorter in duration and more recent than the second time period.

20. The computer-readable medium of claim 19 wherein the instructions include:
- reconfiguring one of the predictive models in response to the one of the predictive models failing validation;
- retraining all of the predictive models including the reconfigured model using the second data; and
- revalidating, subsequent to the retraining, all of the predictive models including the reconfigured model using the first data.

* * * * *